United States Patent
Hoftman et al.

[11] Patent Number: 5,857,569
[45] Date of Patent: Jan. 12, 1999

[54] TWIST UNLOCK AND DOWNWARD PUSH DISENGAGE NEEDLE UNLOCKER SYSTEM

[76] Inventors: Moshe Hoftman, Calabasas; Nir Hoftman, San Francisco, both of Calif.

[21] Appl. No.: 811,200

[22] Filed: Mar. 5, 1997

[51] Int. Cl.[6] .................................................. B65D 83/10
[52] U.S. Cl. .......................... 206/366; 206/365; 206/370
[58] Field of Search .................... 206/366, 370, 206/365, 364; 604/192, 198, 110

[56] References Cited

U.S. PATENT DOCUMENTS

| | | |
|---|---|---|
| 4,092,462 | 5/1978 | Sagstetter et al. . |
| 4,576,281 | 3/1986 | Kirksey . |
| 4,625,877 | 12/1986 | Hoch . |
| 4,802,579 | 2/1989 | Hall et al. . |
| 4,875,265 | 10/1989 | Yoshida .................... 206/366 |
| 4,890,734 | 1/1990 | Gach ........................ 206/366 |
| 5,024,237 | 6/1991 | Shillington . |
| 5,031,767 | 7/1991 | Bruno . |
| 5,092,462 | 3/1992 | Sagstetter et al. . |
| 5,183,156 | 2/1993 | Bruno . |
| 5,265,724 | 11/1993 | Dondlinger ............... 206/366 |
| 5,277,312 | 1/1994 | Vumbaca .................. 206/366 |
| 5,312,346 | 5/1994 | Han . |
| 5,322,164 | 6/1994 | Richardson et al. . |
| 5,402,887 | 4/1995 | Shillington . |
| 5,409,112 | 4/1995 | Sagstetter . |
| 5,409,113 | 4/1995 | Richardson et al. . |
| 5,415,315 | 5/1995 | Ramirez . |
| 5,483,999 | 1/1996 | Lampropoulos et al. ......... 604/192 |
| 5,505,705 | 4/1996 | Galpin et al. .................. 604/192 |
| 5,718,689 | 2/1998 | Stevenson ..................... 206/365 |

FOREIGN PATENT DOCUMENTS

| | | | |
|---|---|---|---|
| 2740335 | 9/1977 | Germany ................... 206/366 |

*Primary Examiner*—David T. Fidel

[57] ABSTRACT

The present invention preferably comprises a method and several apparatus embodiments for needle unlocking and disengagement by a single straight-through insertion of the needle to the needle hub, twist unlocking and push through and pull back disengagement. In addition, it is preferable to adapt the relatively small "footprint" of the needle unlocking and disengagement device for placement at the end of a splash and aerosol protective cylinder whereby the external cylindrical body surface of the syringe or vacuum tube adapter lies relatively close to the inside wall of the protective cylinder upon insertion of the syringe or vacuum tube adapter for needle unlocking and disengagement.

18 Claims, 8 Drawing Sheets

TWIST UNLOCK AND DOWNWARD PUSH DISENGAGE NEEDLE UNLOCKER SYSTEM

BACKGROUND OF THE INVENTION

The present invention relates to a device for removing hypodermic needles from syringes or similar devices.

U.S. Pat. No. 4,576,281 describes a medical container designed to provide a simple method and structure for the disposal of medical needles, of the type for taking blood samples and similar applications. Needles of this type have a steel or metal shank portion through which the blood or liquid is drawn, a plastic collar intermediate the length of the steel shank for releasably engaging a barrel portion with a portion of the needle extending interior to the barrel. The needles are released from the barrel by screwing the plastic collar out of the barrel. The container assists in this operation and includes a needle release area, preferably a sunken recess, which has a needle receiving port having an enlarged area through which the needle and collar may pass and a restricted area for gripping the front portion of the plastic collar hub on the needle. The needle release area is shaped to provide the user with a mechanical advantage by using the barrel portion as a lever, forcing the collar into the restricted area of the needle release area in a manner to grip the collar and hold the same such that the barrel may be rotated to cause release of the needle. After the screw thread of the collar has been released from the barrel, the needle is then passed through the enlarged area, whereupon the needle falls through the enlarged area into the closed confines of the container.

U.S. Pat. No. 4,802,579 describes a vertically upright box-type outer enclosure including a hinged, lockable front door permitting an upwardly open disposable jar container to be locked internally and aligned with a hole within the top of the box-type enclosure. A cylindrical drop chute fits to the hole and is barrel bolt locked in position with its lower end penetrating the top of the jar. The top of the drop chute carries a slotted needle remover plate, with the slot tapering such that a disposable sharp steel plastic needle holder frictionally fit to the lower end of a syringe barrel is inserted within the slot at its enlarged end, moved transversely within the slot such that the plastic needle holder is captured beneath the needle remover plate. The syringe body barrel is moved upwardly detaching the needle therefrom and permitting it to fall by gravity into the sharps impenetrable, jar type container. The door is periodically opened and the jar and accumulated needles removed.

U.S. Pat. No. 5,024,327 describes a limited access closure cover for an opening in a top of a disposable sharps container comprising a frame for securing to the periphery of an open top of a container, an opening in the cover, the opening having the configuration of a cross section axial view of the syringe body, and finger flanges on the syringe body for receiving the axial passage of the body of a hypodermic syringe when angularly oriented to conform thereto.

U.S. Pat. No. 5,031,767 describes a needle removal/containment and transport apparatus for potentially injurious medical implements, generally comprising a storage and transport housing; a storage container slidably inserted within the housing for receiving and storing the implements; a plastic bag surrounding the container; a needle removal device mounted on the container for threadably disengaging needle/syringe assemblies and depositing the needles into the container; and an entry port formed on the container with a releasably insertable plug member for depositing implements such as syringes, scalpels, etc. into the container. The housing is formed with flap members to permanently seal the container within the housing, yet permit access to the container. The housing is further formed with a cover member to permanently sealingly close the housing for transport to ultimate disposal. The needle removal device comprises a plate member formed with a first receiving slot, and an integral needle engaging member comprising a pair of opposed finger members integrated with a base member to form a stepped slot providing a second receiving slot and a contiguous engaging slot. The first receiving slot is laterally aligned with the second receiving slot at an elevation generally higher with respect thereto. The needle hub is slidably translated through the second receiving slot into engagement with the needle removal device via the engaging slot whereupon the syringe can be rotated relative to the needle hub to unthread the needle from the syringe. The unthreaded needle and syringe are then removed from the engaging slot and translated through the second receiving slot and into the first receiving slot such that the needle hub is disposed on the underside of the plate member permitting the needle to drop into the container. In the event the needle has not been fully unthreaded from the syringe or in the case of a multi-sample needle where the needle can hang-up within the syringe, the needle hub will engage the underside of the plate member in response to upward forces applied to the syringe to act as a stop preventing the needle from being pulled out of the removal device.

U.S. Pat. No. 5,092,462 describes a receptacle including a first recess for receiving the anterior end of the barrel of a conventional double ended needle blood collection tube holder to stabilize the holder during threaded disengagement of the needle. A post is disposed within the recess to prevent rotation of the hub while the holder is rotated to unthread the hub. Upon threaded disengagement, the needle drops into the receptacle, which drop may be augmented by a pair of leaf springs. A second recess in the receptacle receives the collar of a guard supporting a translatable blood collection tube holder, which holder threadedly engages the hub of a double ended needle. A post within the recess can extend within the collar to engage a rib of the hub to prevent rotation of the double ended needle upon rotation of the guard to threadedly disengage the hub from the holder. Upon threaded disengagement, the double ended needle drops into the receptacle, which drop may be augmented by a pair of leaf springs.

U.S. Pat. No. 5,183,156 describes a needle removal and storage device comprising a plate member attachable to a suitable container. The plate member is formed with a an engaging slot defined by a pair of opposed finger members. The engaging slot is laterally aligned with a receiving slot disposed at an elevation generally higher with respect thereto. The needle hub is slidably translated through the engaging slot into engagement with the finger members whereupon the syringe can be disengaged from the needle. The disengaged needle and syringe are then removed from the engaging slot and translated into the receiving slot such that the needle hub is disposed on the underside of the plate member permitting the needle to drop into the container. In the event the needle has not been fully unthreaded from the syringe or in the case of a multi-sample needle where the needle can hang-up within the syringe, the needle hub will engage the underside of the plate member in response to upward forces applied to the syringe to act as a stop preventing the needle from being pulled out of the removal device.

U.S. Pat. No. 5,312,346 describes an improved device for removing used needles from reusable syringes. The device may be operated using only one hand and requires a single downward force applied to the syringe body by the health care worker. At the lower end of the downward stroke, the collar of the needle has been twisted off the syringe body and is automatically deposited into the receptacle for used needles. The health care worker releases the force and the apparatus automatically resets itself to receive another used needle. The device has few parts and may be assembled easily.

U.S. Pat. No. 5,322,164 describes a disposal container for automatic release of cannulas from a holder and for disposal of the cannulas, and a system for hands-free release of a cannula from a holder. Included is a disposal container having a release aperture formed in the top, the aperture including opposite tapered sides extending into the container. A cannula is mounted in a cannula holder, the holder having at least one depressible lock element extending from the holder. The holder is inserted in the release aperture with the lock element engaging the tapered side, and the holder is then depressed to automatically eject the cannula from the holder. If the cannula is installed in a removable adapter inserted in the holder, both the adapter and the cannula are ejected when the holder is depressed in the aperture.

U.S. Pat. No. 5,402,877 describes a disposable container closure assembly including a needle removal slot having gear teeth along one side thereof for engaging flutes on a needle hub for rotating the needle relative to a non-rotatable holder passed therealong.

U.S. Pat. No. 5,409,122 describes a needle disposal system has a blood collection holder with an engaged blood collection needle and a companion biohazard receptacle for disposal of the needle after use. First, the blood collection needle engaged to the holder is irreversibly positively locked upon insertion into respective needle removal device of the biohazard receptacle, thereby preventing withdrawal of the needle from the biohazard receptacle. The needle is then unthreaded from the holder and disposed of inside the biohazard receptacle.

U.S. Pat. No. 5,409,113 describes a disposal container for automatic release of cannulas from a holder and for disposal of the cannulas, and a system for hands-free release of a cannula from a holder. Included is a disposal container having a release aperture formed in the top, the aperture including opposite tapered sides extending into the container. A cannula is mounted in a cannula holder, the holder having at least one depressible lock element extending from the holder. The holder is inserted in the release aperture with the lock element engaging the tapered side, and the holder is then depressed to automatically eject the cannula from the holder. If the cannula is installed in a removable adapter inserted in the holder, both the adapter and the cannula are ejected when the holder is depressed in the aperture.

U.S. Pat. No. 5,415,315 describes a container lid for a medical storage-disposal container including a slide closure resistant to inadvertent movement from an open position into a fully closed and locked position. The container lid includes a top cover defining a disposal aperture and a laterally oriented depression. The slide closure contains a descending flange configured to engage the top cover depression and lock the slide closure in a fully closed position. An obstructing tab is pivotally coupled to the top cover and projects into the disposal aperture. The slide closure can only be moved into a fully closed and locked position if the obstructing tab is rotated into a non-obstructing orientation. The slide closure further includes protrusions on opposing lateral sides to require application of an affirmative force in order to displace the slide closure from a fully opened position. The slide enclosure further includes a plurality of straight sided apertures to facilitate removal of protective covers from hypodermic needles of varying size. The top cover further includes an aperture intersecting a tapering slot to facilitate removal of hypodermic needles of varying sizes from syringe bodies.

All prior art devices for removing needles from syringes or cannulas must have the function of only temporarily securing a needle hub for unlocking. The speed, ease of use, safety and low cost of the unlocking device are the goals of the well designed needle unlocking devices. It is apparent from the variety of needle unlocking devices that the search for improvements is current and critical in light of the ease of transmission of chronic and life-threatening diseases through pin pricks from needles as well as splashing and aerosolization of the body fluids that can easily occur in the unlocking and disposal motions.

SUMMARY OF THE INVENTION

The present invention preferably comprises a method and several apparatus embodiments for needle unlocking and disengagement by a single straight-through insertion of the needle to the needle hub, twist unlocking and push through and pull back disengagement. In addition, it is preferable to adapt the relatively small "footprint" of the needle unlocking and disengagement device for placement at the end of a splash and aerosol protective cylinder whereby the external cylindrical body surface of the syringe or vacuum tube adapter lies relatively close to the inside wall of the protective cylinder upon insertion of the syringe or vacuum tube adapter for needle unlocking and disengagement. The end of the cylinder distal to the location of the needle unlocking and disengagement device is sealingly or supportively attached to a support plate and provided with an opening in the support plate through which syringes or vacuum tube adapters may be inserted.

Although the more specific description of the embodiments of the present invention show a wide variation in the manner of achieving

BRIEF DESCRIPTION OF THE DRAWINGS

FIG. 5 shows an alternate embodiment of the device of FIG. 1A whereby the square apertures for hypodermic needle cover storage of various sizes are located in the surface of the removable box cover with relatively short downward rectangular box extensions therefrom to provide support and elimination of the danger of pushing the needle cover through the aperture upon removal or replacement.

DETAILED DESCRIPTION OF THE INVENTION

The present invention is device for removal of hypodermic or venipuncture needles from syringes or vacuum tube adapters. Although several related devices are known to the skilled person in this art, the present invention dramatically improves safety of needle removal while retaining a simple and inexpensive design. The present invention comprises a flat sheet of flexible material, wherein a circular piece of the sheet of flexible material is preferably at least about 0.5 inches across. Flexible material, as used herein, comprises thermoplastic, firm elastomeric or flexible thermoset polymers and plastics. Flexible material also comprises similar materials as required by the objects of the invention described below, and also includes multiple layering of flexible and other materials, as well as locally varying sheet thickness to accomplish those objects. The above minimum diameter is not an absolute lower limit to the diameter of the sheet of flexible material, however is a recommended limit considering the objects of the invention described for an economically efficient design below.

Through the sheet of flexible material an opening is made, preferably in the shape of an "+-cross", "H" or "Y" opening. The width of the cross-member openings of the "+-cross", "H" or "Y" openings in the flexible material must be sufficient to accommodate typical lateral hypodermic needle hub extensions (i.e., on the external surface of the plastic or metal female needle-to-syringe hub adapter needed to fix the needle to a syringe or vacuum tube adapter) when the needle, attached to the syringe or vacuum tube adapter, is inserted into the opening in the flexible material where the "+-cross", "H" or "Y" opening cross-members intersect. The needle thus inserted will "lock" its hub external extensions into the "+-cross", "H" or "Y" opening cross-members. A twisting motion will enable the user to unlock or un-"slip" the needle from the syringe or vacuum tube Luer-lock® or Luerslip® connection to the adapter. It will be preferable make the "+-cross", "H" or "Y" opening cross-members wide enough to accommodate the female adapter extensions, however, at the same time reducing that width so that a hub adapter will, at least at the adapter's widest diameter, make effective, position-fixing contact with the unlocking/downward flexure lugs at the intersection of the "+-cross", "H" or "Y" openings into which the needle has been inserted.

All commercially available needles incorporate such a rim at the syringe insertion opening of the adapter hub, either for use in a Luer®-Lock or similar syringe or just to improve the strength of the hub for use on a slip locking syringe. The objects of the present invention are especially advantageous when such a rim extension on the hub is present.

In a further embodiment of the present invention wherein the sheet of flexible material with its opening and/or other improvements are used, a minimum-diameter circular sheet of flexible material, with its characteristic "+-cross", "H" or "Y" openings extending from its center to just within the diameter of the minimum diameter, will be fixed to a broader support so that it might be more easily used for needle removal. In yet a further embodiment of the present invention, a circular sheet with a minimum diameter of flexible material is sealingly fixed at one end to a relatively short cylindrical splash prevention tube, wherein the diameter of the cylindrical splash prevention tube is just slightly larger than the largest syringe from which needles will be desirably removed by the present invention. The other end of the cylindrical splash prevention tube is preferably fixed to a hole in a support sheet, such that the support sheet can be held in one hand or otherwise be fixed in place while the user inserts a needle in the open end of the cylindrical splash prevention tube through to the intersection of the "+-cross", "H" or "Y" openings in the flexible material until the above-described "locking" of the female needle adapter occurs. The inner wall of the cylindrical splash prevention tube supportably guides and steadies the barrel of the syringe while the needle unlocking or un-"slipping" takes place.

Once the needle has been unlocked or un-"slipped" from the syringe, the syringe has been disengaged from the needle. The user, upon withdrawal of the syringe from the splash prevention tube, would be able to observe that the female needle adapter will still be "locked" in the "+-cross", "H" or "Y" openings of the flexible material, with the needle extending from the outside face of the flexible material at the end of the cylindrical splash prevention tube. The user preferably retains the syringe in the cylindrical splash prevention tube until the user pushes the syringe back onto the top of the hub adapter with sufficient force to flex outwardly the unlocking/downward flexure lugs of the flexible material. When the top rim of the needle hub is pressed beyond the outwardly flexed curved edges of the unlocking/downward flexure lugs, the lugs snap a short distance to the surface of the instrument being used to push the top rim of the needle hub past the unlocking/downward flexure lugs, wherein the needle assembly is entirely separated from both the syringe and the unlocking/downward flexure lugs. It is especially advantageous if the support sheet of this embodiment comprises the top of a box which will receive discarded needle assemblies after they are removed from their syringes.

The present invention is now discussed with reference to the above described Figures. FIG. 1 shows the several outlines of apertures which may be formed from unlocking/downward flexure lugs of the present invention. "+-cross", "H" or "Y" openings are generally shown in apertures 1G–1J, 1A–1F and 1L respectively. Although these apertures are preferred for the present invention, increasing the number of unlocking/downward flexure lugs whose arrangement generally allows needle unlocking without substantial sideways or lateral movement of the needle hub is taught by the present invention. It is seen herein by the skilled person that the "+-cross" openings will have four unlocking/downward flexure lugs, although more may be provided whereby a central intersection of the aperture slots between the lugs is provided for insertion of first the needle shank and then the hub and its lateral extensions.

Figure 1A:
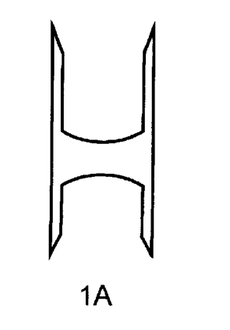
FIG. 1A shows the opening of item 1F of FIG. 1 adapted for secure service in a splash prevention tube which is attached to an opening in the top of a removable box covering including square apertures for hypodermic needle cover storage of various sizes, an aperture for disposal of syringes and vacuum tube adapter covers and a closure covering adapted so that it may be locked downwardly along the box, covering only the syringe disposal aperture or latched securely covering both the syringe disposal aperture and the opening for the splash prevention tube.

FIG. 1A shows a top view of a removable box cover 100 with several embodiments of the present invention. Cover 100 is shown as a preferably substantially square cover with a cover plate 104 with downwardly extending sides 104A. Splash prevention tube opening 101 is made to accommodate the securing of a splash prevention tube, at which opposite end is secured to lug plate 102 defining lug aperture 103, which is substantially similar to that shown in item 1F of FIG. 1. Accommodation for molding and venting for the cover 100 are openings 105. Novel extensions of the bottom side of cover plate 104 will be described later whereby needle shanks (retained in the disposal box to which the cover 100 will be attached) will be prevented from accidentally slipping out of those openings 105 to harm personnel handling the box. A syringe opening 106 is formed in cover plate 104 to permit disposal of syringes or vacuum tube adapters from which needles have been removed.

In FIG. 1A, latches 107 are formed as extensions of cover plate 104 to hold down first closure plate 111 when syringe opening 106 is to be sealed. Flexible, molded hinges 112 preferably attach first closure plate 111 to sides 104A so that first closure plate 111 can be simply folded over the top of cover plate 104 to cover syringe opening 106. Distal to hinges 112 on first closure plate 111 is flexure 115 which provides flexible attachment to second closure plate 111A. Second closure plate 111A further comprises a latch 114, which is inserted into latch receiver 110 (an extension of sides 104A) upon folding over of first and second closure plates 111 and 111A respectively to sealingly close syringe opening 106 and opening 101. Extensions 113 from the first closure plate 111 are made such that when the edges of the first closure plate are pressed below latches 107, those extensions 113 prevent disposed needles from emerging from between the edges of opening 106 parallel to the length of first closure plate 111 and those edges of first closure plate 111. Items in the several Figures with identical item or aspect numbers, have substantially the same or identical functions and configurations. Sides 104 extension 108 provides a set of square apertures 109 for temporary storage of needle covers.

Figure 1B:
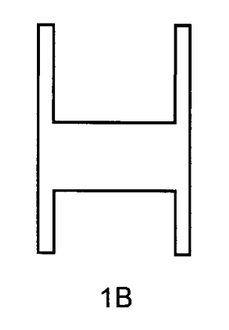
FIG. 1B is a top view of an aperture embodiment with side by side needle unlocking apertures formed in a mounting plate, wherein an effective unlocking width is varied to accommodate, needle hubs with substantially different widths.

FIG. 1B shows a breakout section of cover plate 104 having formed in it side by side needle unlocking apertures 1B and 1B'. It is preferable that the distance between the flexible lugs opposed to each other across those apertures be sufficiently different so that needle hubs of substantially different diameters may be unlocked from their attached syringes in an appropriate manner. It will be clear that the distance between the flexible lugs or tabs of aperture 103 is greater than that of aperture 103'. Aperture 103' is adapted to unlock and have pressed through its associated flexible lugs or tabs the relatively small diameter needle hub of a current product of the Tetumo Corporation, the product name being Venoject®. This relatively new product has a needle hub with a substantially smaller diameter than that of most needle hubs in the prior art. In use, apertures 103 and 103' will preferably have marking or labels below rims 101, 101' or 101" along the walls of the splash tube or on the needle unlocking lugs, or associated close to the portion of plate 104 wherein are formed the apertures 103 and 103', whereby the user will be able to determine which aperture is appropriate for small diameter needle hubs without inspection of the widths between unlocking flexible lugs.

Figure 1C:
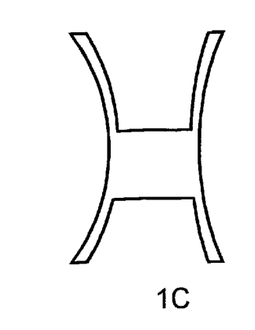
FIG. 1C is a top view of an aperture embodiment accommodating in one aperture needle hubs with substantially different diameters.

FIG. 1C is designed to accommodate unlocking of both standard and small diameter needle hubs in aperture 1M. Lug plate 102 is extended in generally a right triangular shape 102' to reduce the distance between the opposing flexible lugs to distance 103", preferably by about 0.7 mm. It will be appreciated that distance 103" will work to unlock or disengage the smaller diameter needle hubs while providing adequate room for larger diameter needle hubs in the adjacent space between the opposing unlocking lugs.

Figures 1C, 1D:
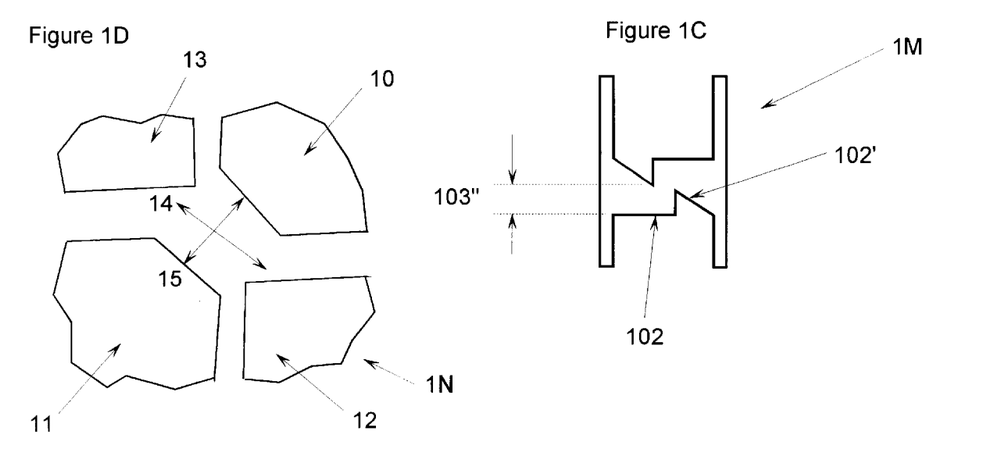
FIG. 1D is a magnified top view of another aperture embodiment accommodating in one aperture needle hubs with substantially different diameters.
Figure 1D:
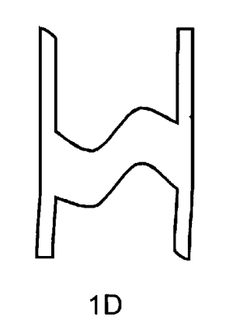
Figure 1E:
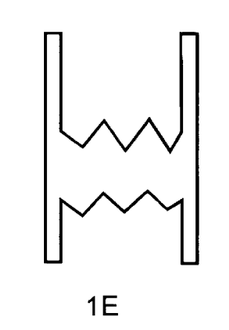
FIG. 1 shows the broad range of configurations of the apertures that will accomplish the objects of the present invention. A "+-cross" opening is represented by items 1G–1K, an "H" opening is represented in items 1A–1F and a "Y" opening is represented in item 1L.
Figure 1F:
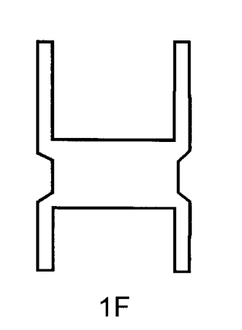
Figure 1G:
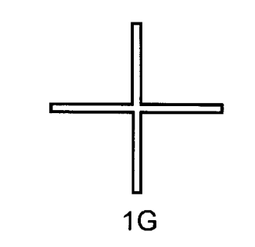
Figure 1H:
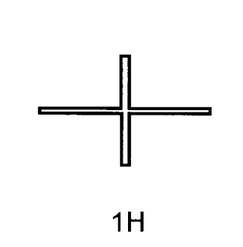
Figure 1I:
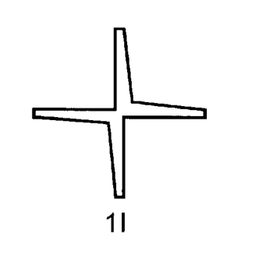
Figure 1J:
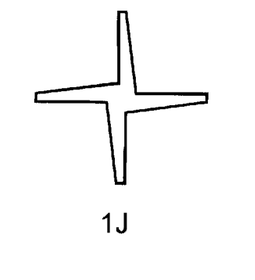
Figure 1K:
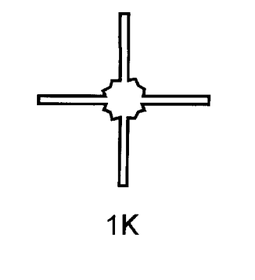
Figure 1L:
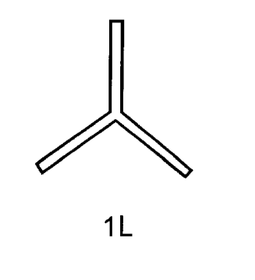

FIG. 1D is also designed to accommodate unlocking of both standard and small diameter needle hubs in aperture 1N. Aperture 1N is shown only in part so that a magnified top view displays the relative location of the four opposed unlocking lugs 10 to 13. The facing edges of lugs 10 and 11 are relatively parallel to each other and describe a distance 15 which is about equal to the diameter of a smaller diameter needle hub or about 2–3 mm. The facing edges of lugs 12 and 13 are substantially pointed and describe a distance 14 which is about equal to the diameter of a larger diameter needle hub or about 3–4 mm.

Figure 2:
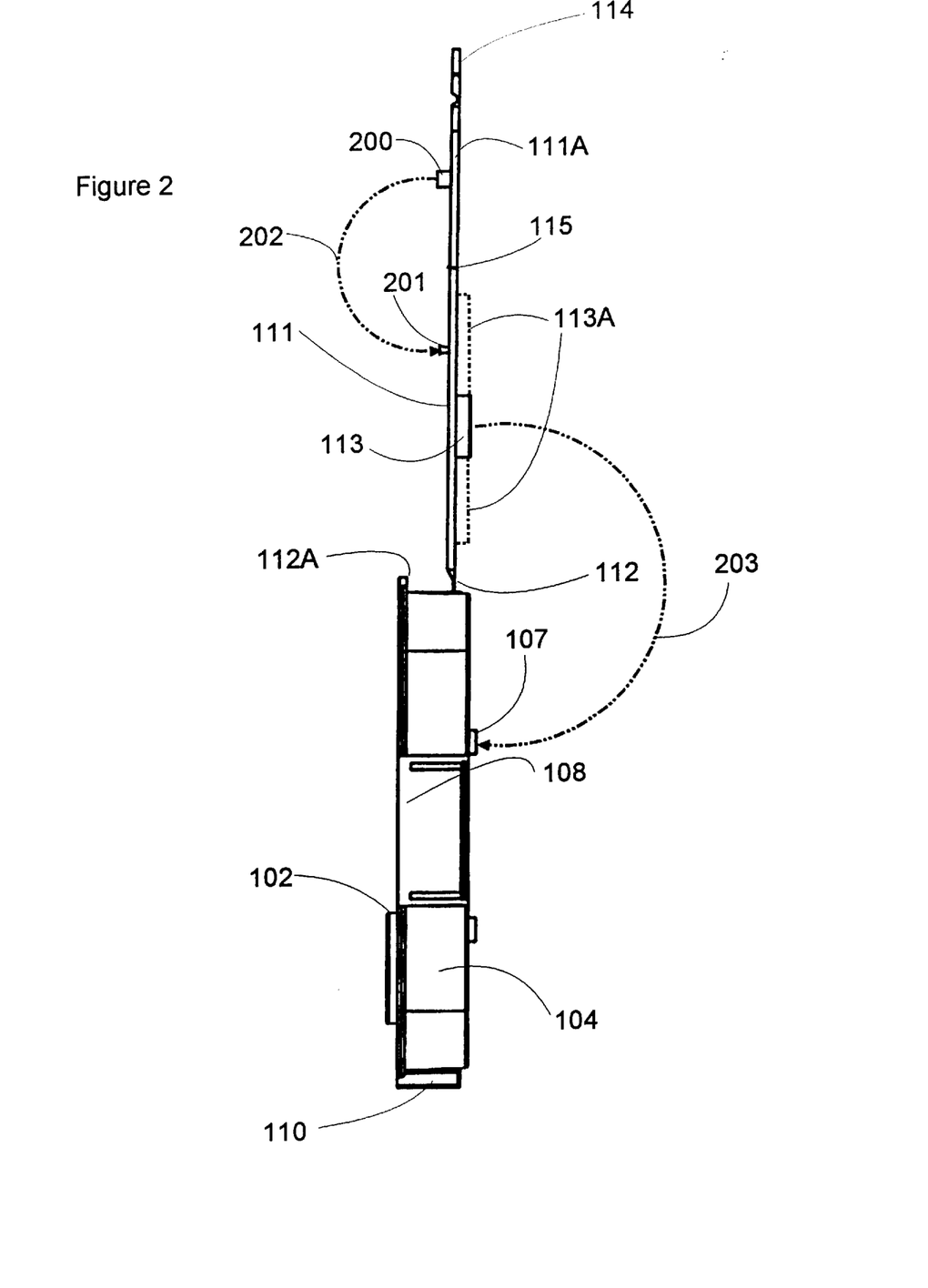
FIG. 2 shows a side view of FIG. 1A and thereby enabling depiction of the various closure paths of the closure covering shown in FIG. 1A.

FIG. 2 shows a side view of FIG. 1A. Extensions 113 may be advantageously and preferably extended as shown to additional extensions 113A. Path 203 describes the closure path of first closure plate 111 such that it may be secured by latches 107. Flexure 115 permits independent closure of the syringe opening 106 with first closure plate 111 while leaving open access to the splash prevention tube and/or lug plate 102 for removal of needles. Path 202 describes the latching path whereby latch receiver 200 on the top side of second closure plate 200 is brought into latching reception with latch 201 on the top of first closure plate 111. Thus, the tendency of the flexure 115 to cause second closure plate 111A to fall over and cover the opening of the splash prevention tube on cover plate 104 is restrained when first closure plate 111 is latched to latches 107.

Figure 3:
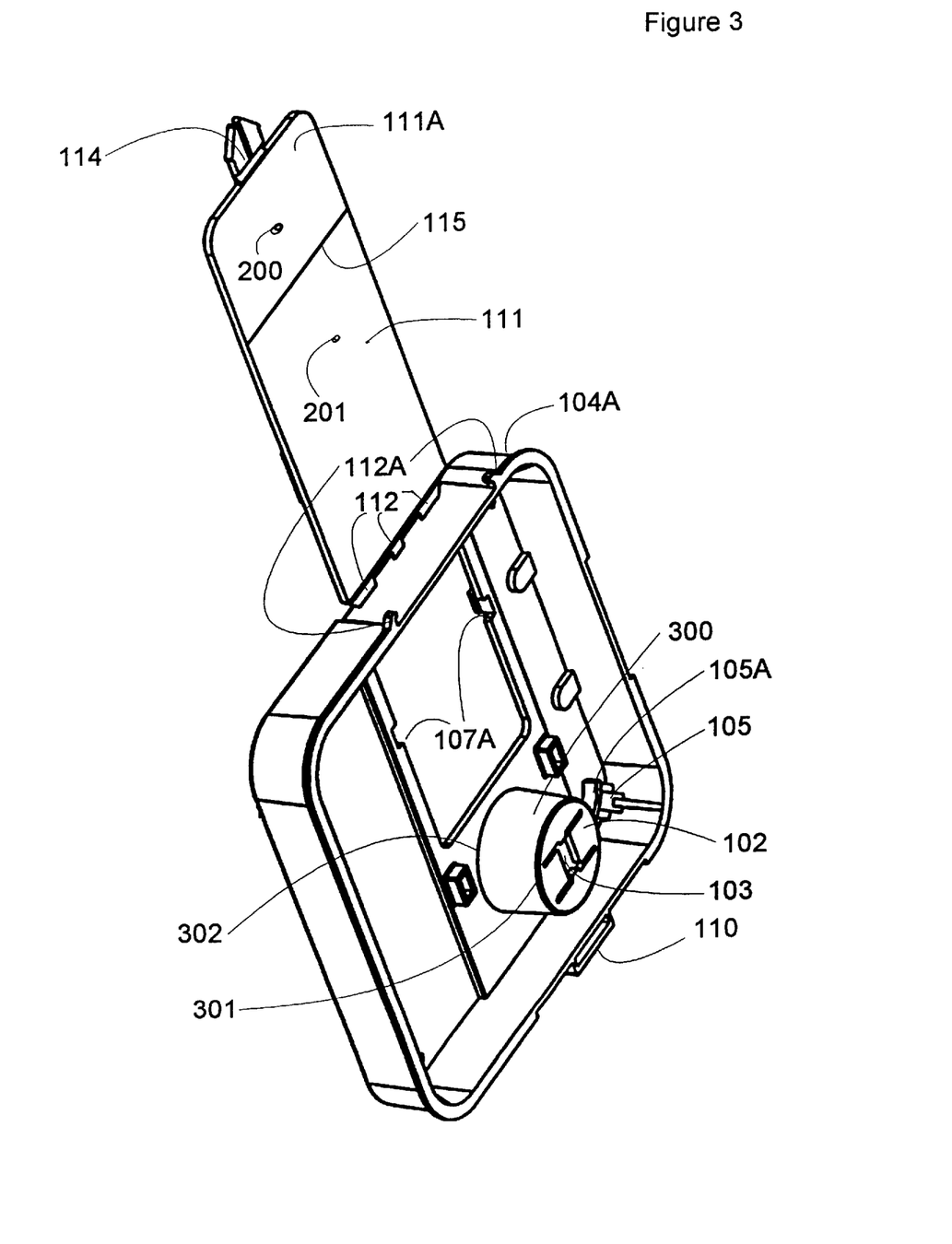
FIG. 3 shows a bottom view of the removable box cover shown in FIG. 1A, enabling an oblique angle view of the splash prevention tube and various smaller openings and needle blocking lugs, whereby the needle blocking lugs prevent accidental exposure of personnel to the points of previously disposed needles.
Figure 4:
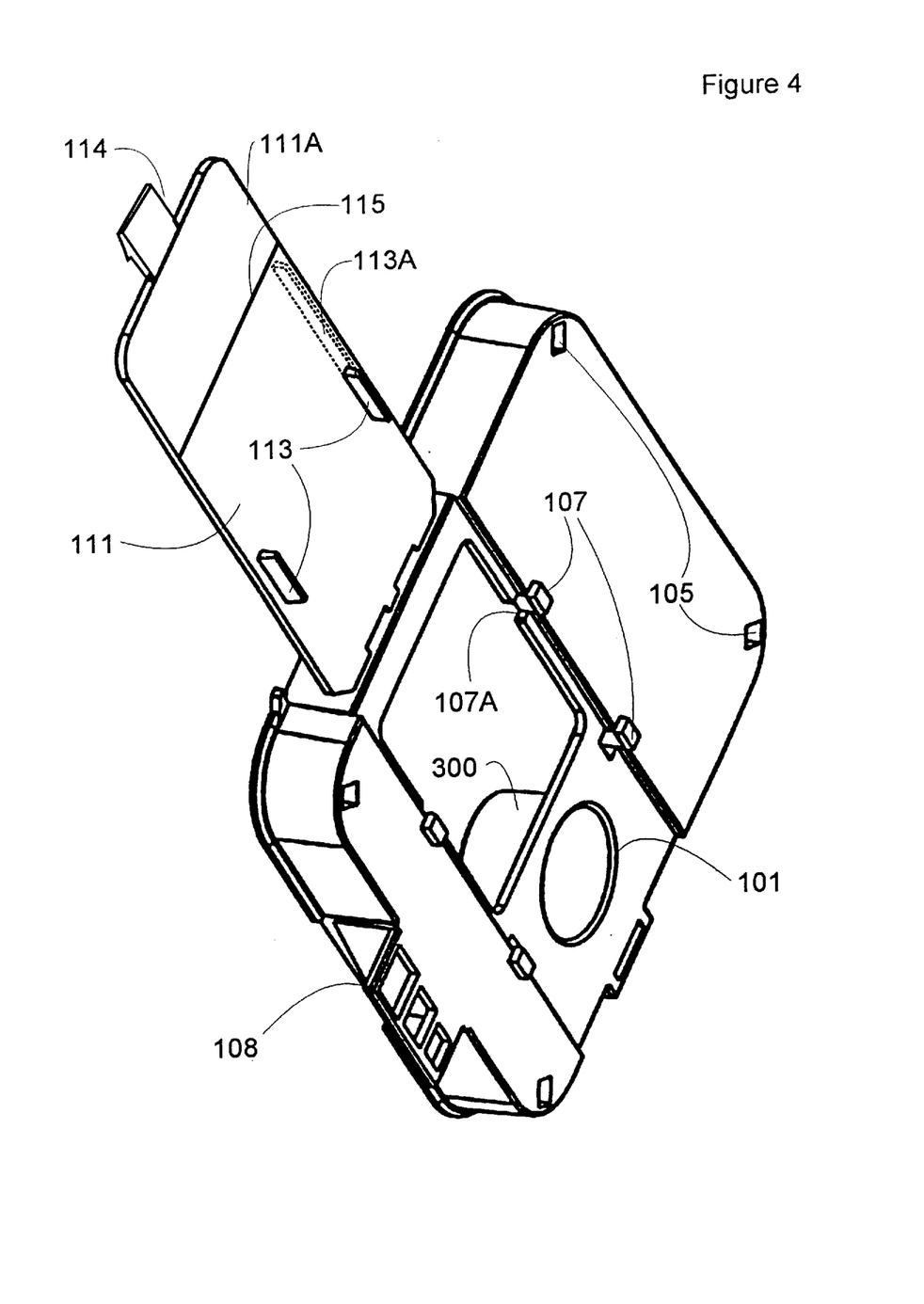
FIG. 4 shows an oblique angle view of the top of the device shown in FIG. 1A, whereby the latching lugs of for the closure covering are more easily seen.

FIGS. 3 and 4 shows bottom and top, respectively, oblique angle views of the removable cover of FIGS. 1A and 2. Splash prevention tube 300 is shown extending from cover plate attachment 302 to lug plate 120 attachment 301.

Figure 5A:
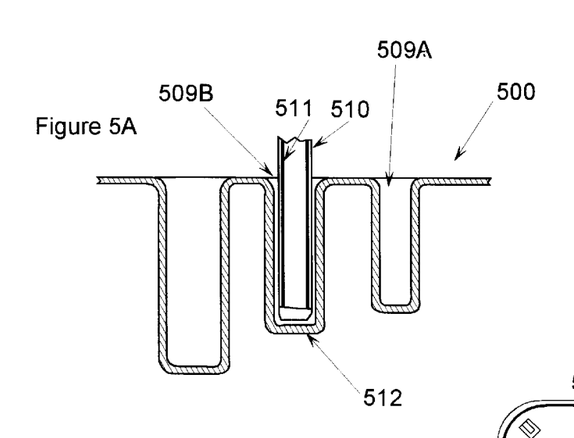
FIG. 5A shows FIG. 5's cross section AA, a side view of needle cover unlocking and support slots.

FIG. 5 shows a further embodiment of the present invention. The removable box cover 500 is substantially the same as shown in FIGS. 1A, 2, 3 and 4 with the following exception. The square apertures 109 of FIG. 1A are moved to a location on the top of the box cover. Square apertures 509 of FIG. 5 have substantially the same dimensions as those of square apertures 109 in Figure 1A. However, square apertures 509 of FIG. 5 have extending downward therefrom (beneath the bottom side of the box cover) boxes with lateral cross-sections equal to the square apertures 509 and provided with a box end to provide isolation of the needle cover placed in the square cross-section box from the contents disposed of beneath the box cover shown in FIG. 509. In addition, the length of the box extensions of square apertures 509 is preferably less than the length of the needle covers to provide a non-binding removal and replacement means for the needle cover, as contrasted to the prior art devices. Cross section AA is shown in FIG. 5A wherein medium needle cover holder 509B is shown supporting needle cover 510 such that cover extensions 511 engage the sides of holder 509B to permit twisting disengagement of needle cover 510 from a needle attached to a syringe (not shown). It will be appreciated that needle cover 510 is shown without its top portion, but that at least a portion of needle cover 510 extends supported on bottom 512 above plate 504 to enhance grasping retrieval of the needle cover 510 when it is needed. Holder 509A is preferably located next to small needle cover holder 509A.

Figure 5B:
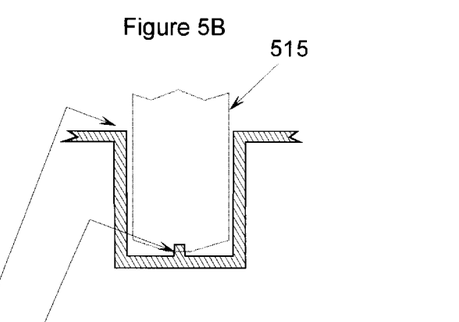
FIG. 5B shows FIG. 5's cross section BB, a side view of Vacutainer® needle holder support and temporary storage means.

A further improvement of the system of the present invention is shown in FIGS. 5 and 5B. Vacutainer® vacuum tubes are filled by insertion onto a second end of a needle sharpened at two ends, the first end having first been inserted into the target body conduit. The two-ended needle is supported at a threaded mid-section by a tubular needle support that supports about half the length of the Vacutainer® tube. These tubular needle supports, outlined as the broken line of tubular needle support 515 in FIG. 5B, may be placed in cylindrical support 513, whose open upper rim is sealingly attached to plate 504 to permit temporary storage of the tubular needle support. Post 514 is preferably located at a bottom closed end of cylindrical support 513, passing through the support opening for the threaded support of a two ended needle. Thus the system shown in FIG. 5 permits the user to first disengage the needle cover of two ended needle in one of the square apertures 509, draw body fluids into a Vacutainer® and withdraw it from the tubular needle support, unlock/push disengage the two ended needle into a sharps container through the action of opposing lugs 502, and store the tubular needle support in cylindrical support 513.

Figure 6:
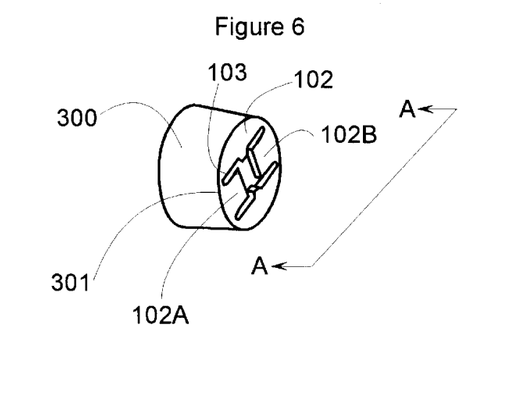
FIG. 6 shows the splash prevention tube and small footprint support plate for the lug arrangement of the present invention, as shown in FIG. 3. Cross-section direction A—A defines the general cross-section of the splash prevention tube and unlocking/downward flexure lugs of the needle unlocking aspect of the present invention as further shown in FIGS. 7, 8 and 9.

FIG. 6 shows the splash prevention tube 103 associated with lug plate 102. Unlocking/downward flexure lugs 102A and 102B of lug plate 102 are representative in the A—A cross-sections shown in FIGS. 7, 8 and 9 of the unlocking/downward flexure lugs which have previously shown to be adapted to form " +-cross", " H" or " Y" openings to accomplish the objects of the present invention.

Figure 7:
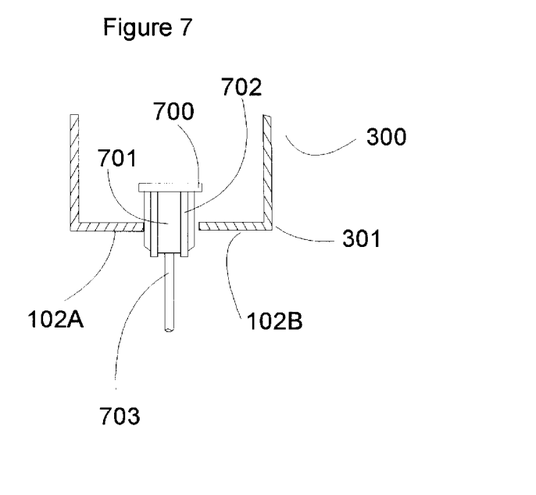
FIG. 7 shows a general adaptation of the unlocking/ downward flexure lugs of the present invention in cross-section. The cross-sections shown in FIGS. 7, 8 and 9 are representative of the unlocking/downward flexure lugs which define the aperture outlines shown in FIG. 1.

FIG. 7 shows a needle hub located between the unlocking/downward flexure lugs 102A and 102B. At this point in the unlocking operation of the present invention, a syringe or vacuum tube adapter is engaged or locked (though not shown) in the needle hub after the needle shank 703 is inserted into the intersection point of the apertures formed by the " +-cross", " H" or " Y" openings of the present invention, whereby the insertion continues until one or more of the hub lateral extensions 702 are securingly locked into one of the aperture extensions from the aperture intersections of the " +-cross", " H" or " Y" openings while the hub top rim 700 remains above unlocking/downward flexure lugs 102A and 102B. It will be seen that a central hub 701 defines a preferred distance slightly smaller than the space between the ends of unlocking/downward flexure lugs 102A and 102B. Providing this distance between the ends of the unlocking/downward flexure lugs improves the resistance to twisting along the axis of the needle and syringe or vacuum tube adapter when the hub lateral extensions 702 are in place as just described. Twisting of the syringe or vacuum tube adapter then unlocks the needle hub from the syringe or vacuum tube adapter.

Figure 8:
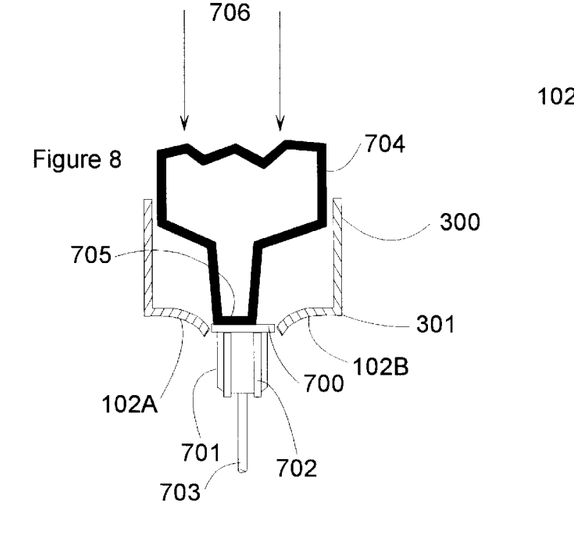
FIG. 8 shows the downward flexure of the unlocking/ downward flexure lugs of the present invention with sufficient downward flexure to accommodate the passage of the top rim of the hub of a hypodermic needle.

FIG. 8 shows the next step in the unlocking and disposal process, as downward pressure from the syringe or vacuum tube adapter is applied onto the hub top rim 700, forcing it through unlocking/downward flexure lugs 102A and 102B. Pressure is applied until the hub top rim escapes securing engagement with unlocking/downward flexure lugs 102A and 102B and the needle assembly drops into a receiving box or receptacle for further handling or disposal. The syringe or vacuum tube adapter is withdrawn from between the unlocking/downward flexure lugs 102A and 102B or may be left in place if preferred. The splashing and aerosoling of body fluids or dangerous drugs (such as radioactive compounds) is eliminated with the splash prevention tube 300 and its length and/or diameter is adapted to meet the requirements of the several types of syringes to be used. In the alternative, lug plate 102 may simply be made integral with cover plate 104 with no splash protection, although adapting lug plate 102 to a splash prevention tube is preferred for the present invention. Syringe 704 in FIG. 8 is shown disengaged from the central hub 701 and pressing the disengaged needle downward in direction 706 at needle engagement tip 705. It will be appreciated that needle engagement tip 706 can be substantially different in configuration than that shown in FIG. 8, such as for Luer®-lock or vacuum tube adapters (i.e., tubular needle supports), and still accomplish the objects of the present invention. One of the most important of the advances made by the present invention is the elimination of side to side motion necessary for locking engagement of prior art needle unlockers. Such side to side motion with surfaces made slippery by water or body fluids increases the risk of slipping and injuring personnel during the needle unlocking and disposal operation. A needle hub engaged to a vacuum tube adapter or syringe will be referred to herein as a device-attached needle hub, being construed to mean needle hubs with a cross sectional profile exhibiting lateral extensions from the hub or other such means to effect unlocking by twisting motion, as with square cross section needle hubs or the like, and engaged to relatively rigid devices for injection or withdrawal of fluids. It will be understood from the above disclosure that needle unlocking and disengagement is performed by facing edges spaced apart such that insertion of the needle hub into the aperture between the facing edges is done without substantial effort. It is preferred that the splash shield described above have a passage length of less than about one inch shorter than a syringe barrel, or other device barrel, such that the unlocking operation is capable of being performed in with the device inserted in the splash shield and about an inch or more of the device barrel will project from the open end of the splash shield for grasping, turning and pushing to accomplish unlocking and disengagement.

Figure 9:
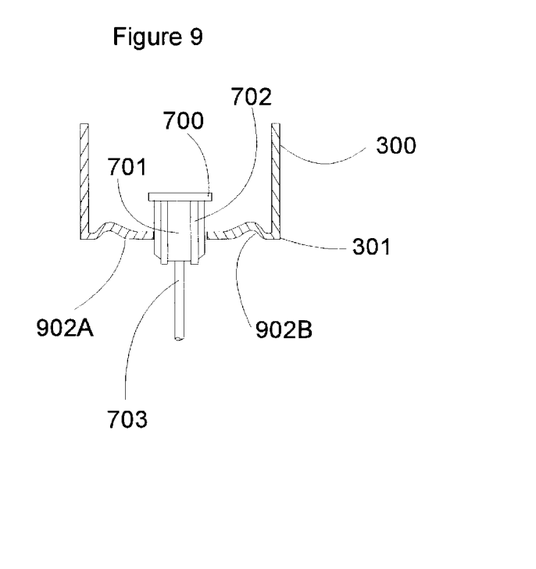
FIG. 9 shows an alternate cross-section construction for the unlocking/downward flexure lugs of the present invention with a stress-fracture reducing annular indentation in those lugs.

FIG. 9 shows an improved, stress relieved embodiment of the unlocking/downward flexure lugs. Unlocking/downward flexure lugs 902A and 902B generally obtain an improved downward flexure life with the U-type indentation in lug plate 102 shown in FIG. 9.

The above options will sometimes present the designer with considerable and wide ranges from which to choose appropriate modifications for the above examples. However, the objects of the present invention will still be obtained by the skilled person applying such options in an appropriate manner.

We claim:

1. A needle unlocker comprising:

two or more unlocking, downward flexure lugs extending substantially toward each other in a plane from a lug plate, wherein adjacent edges of the lugs define an aperture with an intersection spacing smaller than a needle hub top rim diameter.

2. The needle unlocker of claim 1 wherein four unlocking, downward flexure lugs define an aperture with substantially a +-cross shaped opening.

3. The needle unlocker of claim 1 wherein two unlocking, downward flexure lugs define an aperture with substantially an H shaped opening.

4. The needle unlocker of claim 1 wherein three unlocking, downward flexure lugs define an aperture with substantially a Y shaped opening.

5. The needle unlocker of claim 1 wherein four unlocking, downward flexure lugs define an aperture with substantially a +-cross shaped opening, wherein two adjacent edges directly opposite each have straight, parallel edges defining an aperture distance substantially less than the aperture distance defined by two other adjacent edges directly opposite each other whose adjacent edges are substantially pointed.

6. The needle unlocker of claim 1 wherein two unlocking, downward flexure lugs define an aperture with substantially an H shaped opening, wherein each adjacent edge directly opposite another adjacent edge additionally comprises a single triangular projection toward the other adjacent edge reducing aperture width over substantially less than the entire width of the adjacent edge.

7. The needle unlocker of claim 6 wherein aperture width is reduced by the triangular projection by about 0.7 mm.

8. The needle unlocker of claim 1 wherein unlocking, downward flexure lugs are adapted to be sufficiently stiff to resist an unlocking twisting motion from a device-attached needle hub and flexible enough such that pushing of an unlocked needle hub rim past the unlocking, downward flexure lugs may be accomplished with hand pressure.

9. The needle unlocker of claim 1 wherein unlocking, downward flexure lugs are supportively attached to and substantially close a first end of two ends of a splash shield conduit additionally comprising a passage shorter than the length of a device of a device-attached needle and open at a second end, wherein the second end and passage are adapted to supportively permit insertion of the device for unlocking and disengagement of the device-attached needle from the device.

10. The needle unlocker of claim 9 wherein a lateral cross section of the passage is substantially the shape as a lateral cross section of the device and a lateral diameter of the passage is slightly larger than a lateral diameter of the device.

11. The needle unlocker of claim 10 wherein the lateral cross section of the device is circular and the passage is longitudinally shorter than a device barrel by at least about one inch.

12. The needle unlocker of claim 9 wherein the second end of the splash shield conduit is supportively attached at its rim to an opening in a removable top for a sharps container such that the splash shield conduit projects into the sharps container.

13. The needle unlocker of claim 12 wherein the sharps container additionally comprises a large opening in its removable top, the large opening being adapted to permit disposal of large objects into the sharps container and is located next to the second end opening of the splash shield conduit such that a door is adapted to latchably completely close those two openings from re-emergence of needle points from the sharps container.

14. The needle unlocker of claim 13 wherein the door comprises a flexible plastic hinged between a zone described at latchable closure of the door over the two openings, the zone being that part of the door just above and between the large opening and the second end opening of the splash shield conduit, and adapted to releasably open the door above the second end opening of the splash shield conduit while latchably completely closing the door above the large opening.

15. The needle unlocker of claim 13 wherein the removable top comprises latching means on the top thereof adapted to secure the door to the removable top on closure over the two openings, the latching means further comprising shield means for latch apertures associated with the latching means, whereby the shield means are adapted to prevent re-emergence of needles from the sharps container.

16. A method for needle unlocking and disengagement comprising:

(a) two or more unlocking, downward flexure lugs extending substantially toward each other in a plane from a lug plate, wherein adjacent edges of the lugs define an aperture with an intersection spacing smaller than a needle hub top rim diameter;

(b) inserting a device-attached needle hub into the aperture;

(c) unlocking and disengaging the needle from a device to which it is attached by twisting motion without substantial lateral motion to engage the unlocking, downward flexure lugs; and (d) pushing past adjacent edges the needle hub top rim by flexure of the unlocking, downward flexure lugs, whereby the needle is released entirely from engagement with unlocking, downward flexure lugs.

17. A system for needle unlocking and disengagement within a removable top for a sharps container comprising:

(a) a needle unlocker with two or more unlocking, downward flexure lugs extending substantially toward each other in a plane from a lug plate, wherein adjacent edges of the lugs define a needle unlocking aperture with an intersection spacing smaller than a needle hub top rim diameter.

18. A system for needle unlocking and disengagement of claim 17 wherein:

(b) a large opening associated closely with the needle unlocker and a door for completely closing the large opening and needle unlocker aperture from re-emergence of needle points;

(c) needle cover unlocking and support means comprising one or more two-end conduits adapted to extend into the sharps container from one open end at the removable top and a closed end at the other end, whereby a needle cover will be supported with its top above the level of the removable top; and (d) a vacuum tube adapter holding conduit comprising a conduit adapted to extend into the sharps container from one open end at the removable top and a closed end at the other end, whereby a vacuum tube adapter will be supported with its top above the level of the removable top.

\* \* \* \* \*